(12) United States Patent
Osborne (10) Patent No.: US 9,027,721 B1
(45) Date of Patent: May 12, 2015

(54) NURSE'S TRAVEL BAG

(76) Inventor: Sharee Osborne, Lorena, TX (US)

(*) Notice: Subject to any disclaimer, the term of this patent is extended or adjusted under 35 U.S.C. 154(b) by 508 days.

(21) Appl. No.: 13/406,573

(22) Filed: Feb. 28, 2012

(51) Int. Cl.
*A45C 5/06* (2006.01)
*A45C 13/00* (2006.01)
*A45C 13/10* (2006.01)

(52) U.S. Cl.
CPC ............... *A45C 5/06* (2013.01); *A45C 13/001* (2013.01); *A45C 13/1038* (2013.01)

(58) Field of Classification Search
USPC .......... 190/101, 18 A, 115, 109–111, 18, 107
See application file for complete search history.

(56) References Cited

U.S. PATENT DOCUMENTS

| 1,360,532 | A | * | 11/1920 | Isaacs et al. | 190/16 |
|---|---|---|---|---|---|
| 2,623,566 | A | * | 12/1952 | Kibler | 190/125 |
| 2,744,621 | A | * | 5/1956 | Kegevic | 312/293.2 |
| 4,793,508 | A | * | 12/1988 | Thompson | 220/533 |
| 4,852,293 | A | * | 8/1989 | Levine et al. | 43/54.1 |
| 5,526,907 | A | * | 6/1996 | Trawick et al. | 190/111 |
| 5,639,004 | A | * | 6/1997 | Carlton et al. | 224/579 |
| 5,676,223 | A | * | 10/1997 | Cunningham | 190/109 |
| 5,799,791 | A | * | 9/1998 | Harley | 206/478 |
| 6,345,709 | B1 | * | 2/2002 | Cheng | 190/119 |
| 6,821,019 | B2 | * | 11/2004 | Mogil | 383/110 |
| 8,011,484 | B2 | * | 9/2011 | McIntyre | 190/110 |
| 2005/0056511 | A1 | * | 3/2005 | Hsieh | 190/125 |

* cited by examiner

*Primary Examiner* — Tri Mai (57) ABSTRACT

The nurse's travel bag is a travel bag or suitcase for storing a plurality of medical devices and/or supplies that a nurse may need. The nurse's travel bag includes a suitcase with a plurality of compartments integrated inside of and along the exterior of the suitcase. Each storage compartment consists of a clear plastic storage compartment, an identifying label, and a zipper for opening and closing said compartment. The suitcase may include rollers and a telescoping handle, which enable rolling of said suitcase. The suitcase includes a collapsible cooler and sharps container that extend from opposing side surfaces, and enable storage therein.

5 Claims, 7 Drawing Sheets

NURSE'S TRAVEL BAG

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

A. Field of the Invention

The invention relates to the field of travel bags, more specifically, a travel bag that is suited for storing a plurality of medical supplies for a nurse.

B. Discussion of the Prior Art

As will be discussed immediately below, no prior art discloses a travel bag or suitcase, which is uniquely adapted for the storage of supplies relating to the delivery of nurse services; wherein the travel bag or suitcase includes a plurality of compartments integrated inside of and along the exterior of the bag or suitcase; wherein each storage compartment consists of a clear plastic storage compartment, an identifying label, and a zipper for opening and closing said compartment; wherein the suitcase may include rollers and a telescoping handle to enable mobilization.

The Wolter at al. Patent Application Publication (U.S. Pub. No. 2004/0149600) discloses an organization and travel bag that features a core storage area and a storage area for a plurality of relatively small articles such as medical supplies. However, the organization and travel bag does not resemble a modified suitcases within which each compartment is specifically designed for a specific medical supply or purpose.

The Luebcke Patent (U.S. Pat. No. 4,241,833) discloses a paramedic kit having multiple storage compartments. However, the paramedic kit of the Luebcke Patent does not resemble a traditional suitcase in which a plurality of compartments is provided for specific medical supplies or purposes.

The Spruiell Patent (U.S. Pat. No. 7,086,397) discloses an emergency medical kit. However, the emergency medical kit is directed to providing a tank with breathing oxygen and does not resemble a traditional suitcase with compartments for storing specific medical supplies.

The Thomas Patent (U.S. Pat. No. 4,513,866) discloses an emergency medical pack having pockets for medical equipment which are arranged such that all of the equipment can be accessed in confined spaces when the pack is in the half-open position. However, the emergency medical pack does not resemble a traditional suitcase, and does not open as such.

The Horn Patent (U.S. Pat. No. 5,848,700) discloses an emergency medical kit that includes a carrying case of approximately briefcase or smaller suitcase size with the upper and lower sections divided into a large number of compartments by insertion of a plastic organizer. Each compartment is directed to a particular medical emergency and is so identified on its cover or lid. The reverse side of the compartment cover has instructions for treating that particular emergency, while the compartment contains the necessary items for that particular emergency.

The Smith Patent (U.S. Pat. No. Des. 291,149) illustrates a design for an emergency bag, which does not depict the interior with any compartments for storing medical supplies or devices.

The Eagles Patent (U.S. Pat. No. 2,289,254) discloses a portable refrigerator bag having a compartment for insertion of a coolant. However, the refrigerator bag does not store a plurality of medical devices and/or supplies via a plurality of individual compartments contained therein.

While the above-described devices fulfill their respective and particular objects and requirements, they do not describe a travel bag or suitcase, which is uniquely adapted for the storage of supplies relating to the delivery of nurse services; wherein the travel bag or suitcase includes a plurality of compartments integrated inside of and along the exterior of the bag or suitcase; wherein each storage compartment consists of a clear plastic storage compartment, an identifying label, and a zipper for opening and closing said compartment; wherein the suitcase may include rollers and a telescoping handle to enable mobilization. In this regard, the nurse's travel bag departs from the conventional concepts and designs of the prior art.

SUMMARY OF THE INVENTION

The nurse's travel bag is a travel bag or suitcase for storing a plurality of medical devices and/or supplies that a nurse may need. The nurse's travel bag includes a suitcase with a plurality of compartments integrated inside of and along the exterior of the suitcase. Each storage compartment consists of a clear plastic storage compartment, an identifying label, and a zipper for opening and closing said compartment. The suitcase may include rollers and a telescoping handle, which enable rolling of said suitcase. The suitcase includes a collapsible cooler and sharps container that extend from opposing side surfaces, and enable storage therein.

These together with additional objects, features and advantages of the nurse's travel bag will be readily apparent to those of ordinary skill in the art upon reading the following detailed description of presently preferred, but nonetheless illustrative, embodiments of the nurse's travel bag when taken in conjunction with the accompanying drawings.

In this respect, before explaining the current embodiments of the nurse's travel bag in detail, it is to be understood that the nurse's travel bag is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the nurse's travel bag.

It is therefore important that the claims be regarded as including such equivalent construction insofar as they do not depart from the spirit and scope of the nurse's travel bag. It is also to be understood that the phraseology and terminology employed herein are for purposes of description and should not be regarded as limiting.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE EMBODIMENT

Detailed reference will now be made to a main embodiment of the present invention, examples of which are illustrated in FIGS. 1-6. A nurse's travel bag 100 (hereinafter invention) includes a suitcase 101 defined by a front surface 102, a rear surface 103, and opposing side surfaces 104. The front surface 102 attaches to one of the two opposing side surfaces 104, and opens therefrom to expose an interior 105 of the suitcase 101.

Figure 3:
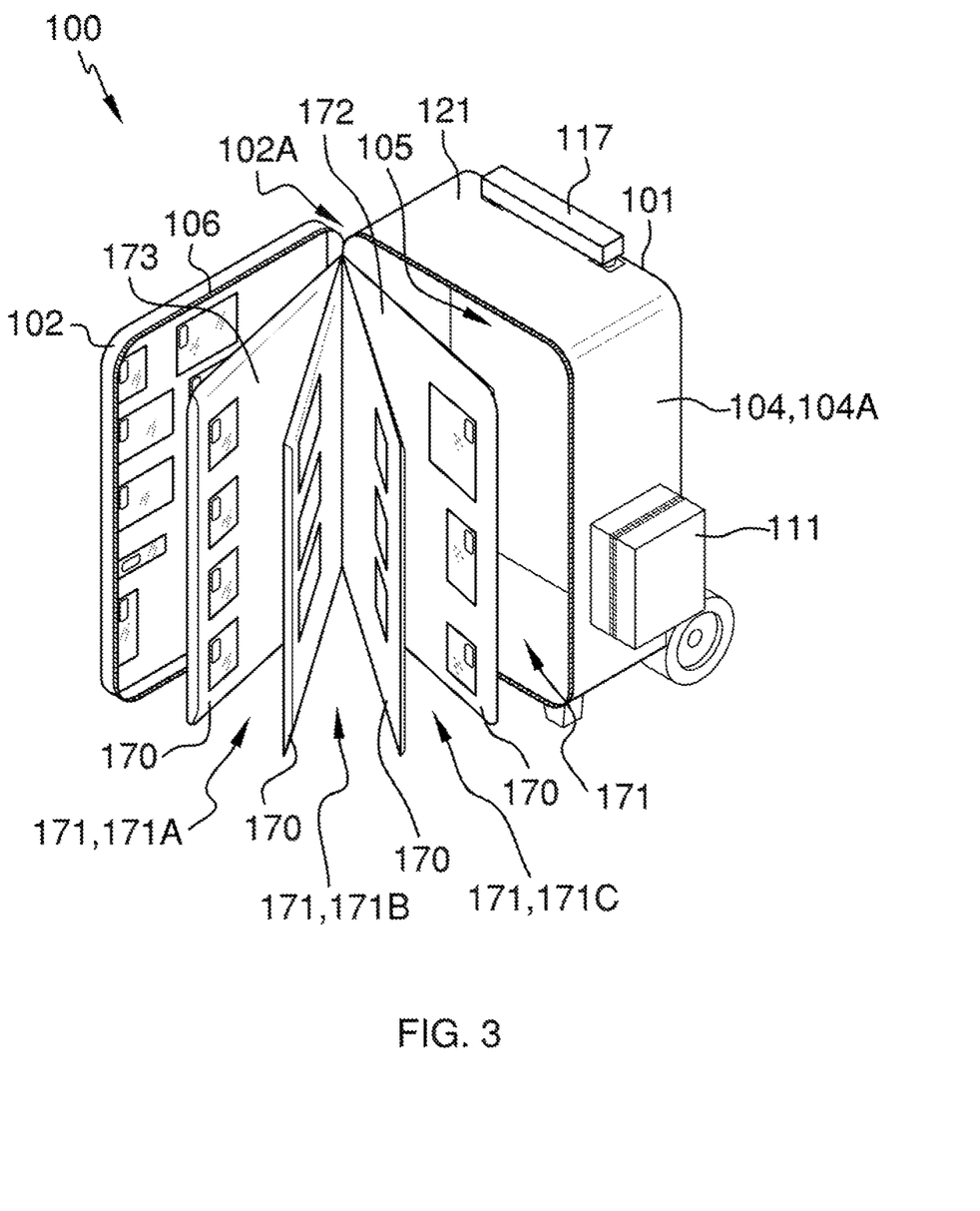
FIG. 3 illustrates a front, perspective view of the nurse's travel bag in which the suitcase is opened to reveal the various compartments that are divided via dividers that attach along the hinge portion of the suitcase.

A zipper 106 extends along 3 of the four edges defining the front surface 102, and unzips to enable the front surface 102 to rotate outwardly with respect to the remaining portions of the suitcase 101, and thereby enabling access to the interior 105 (see FIG. 3). Moreover, the front surface 102 is permanently affixed along a side edge 102A to the respective opposing side surface 104.

Figure 1:
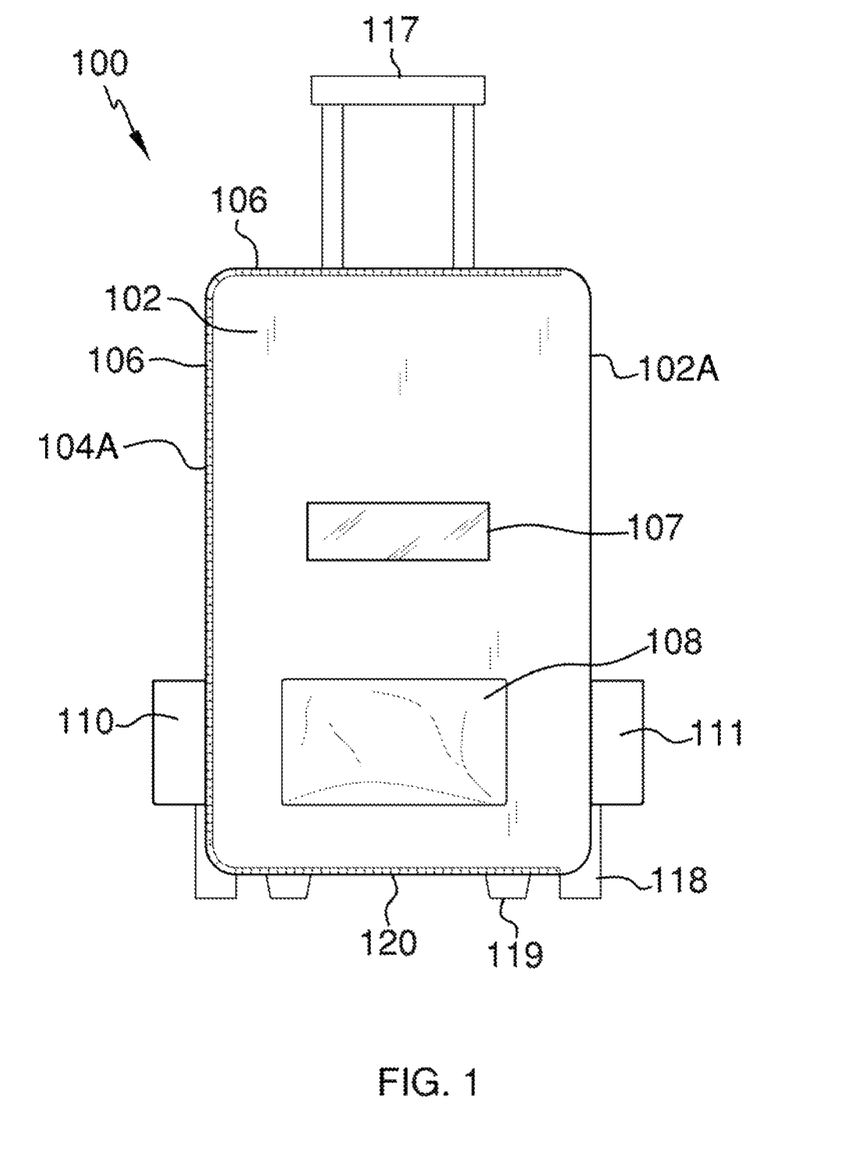
FIG. 1 illustrates a front view of the nurse's travel bag in which the collapsible cooler and sharps container extend from opposing side surfaces of the suitcase.

Located on the front surface 102 of the invention 100 is a name label 107, which provides a place to insert a label identifying ownership of the invention 100. The front surface 102 also includes a front pocket 108, which enables objects to be placed therein.

Figure 2:
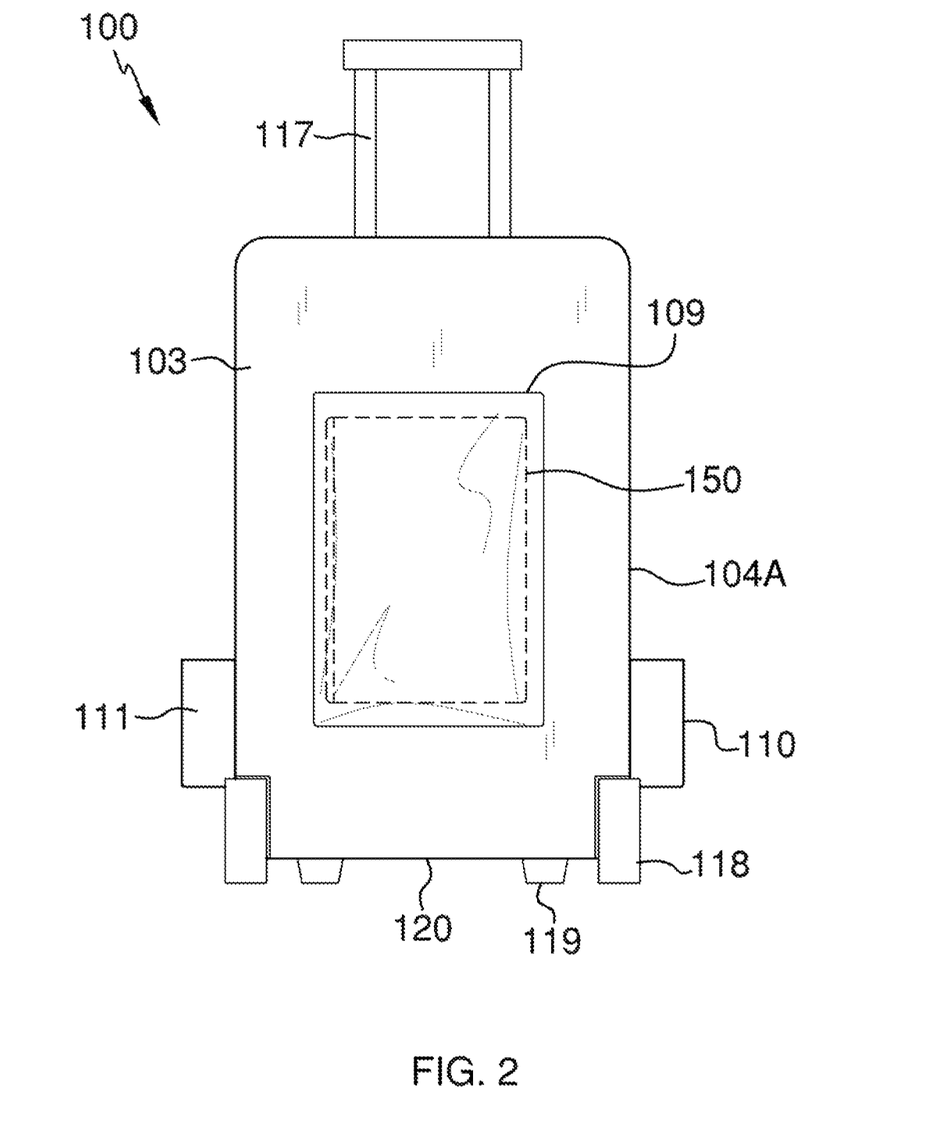
FIG. 2 illustrates a rear view of the nurse's travel bag in which a pocket is integrated into a rear surface of the suitcase, and which supports a laptop computer or paperwork therein.

Located on the rear surface 103 is a rear pocket 109, which shall enable a laptop computer 150 to be inserted therein.

The opposing side surfaces 104 may be further classified as a first opposing side surface 104A and a second opposing side surface 104B. The first opposing side surface 104A includes a sharps container 110. The sharps container 110 extends outwardly from the first opposing side surface 104A, and enables used sharp objects, such as used needles, to be inserted therein. Located on the second opposing side surface 104B is a collapsible cooler 111. The collapsible cooler 111 extends outwardly from the second opposing side surface 104B, and provides an insulated place within which to store objects therein at a chilled temperature. It shall be noted that the collapsible cooler 111 is included with the invention 100 in that the invention 100 can store items that require chilling or refrigeration, such as medicines.

Figure 3A:
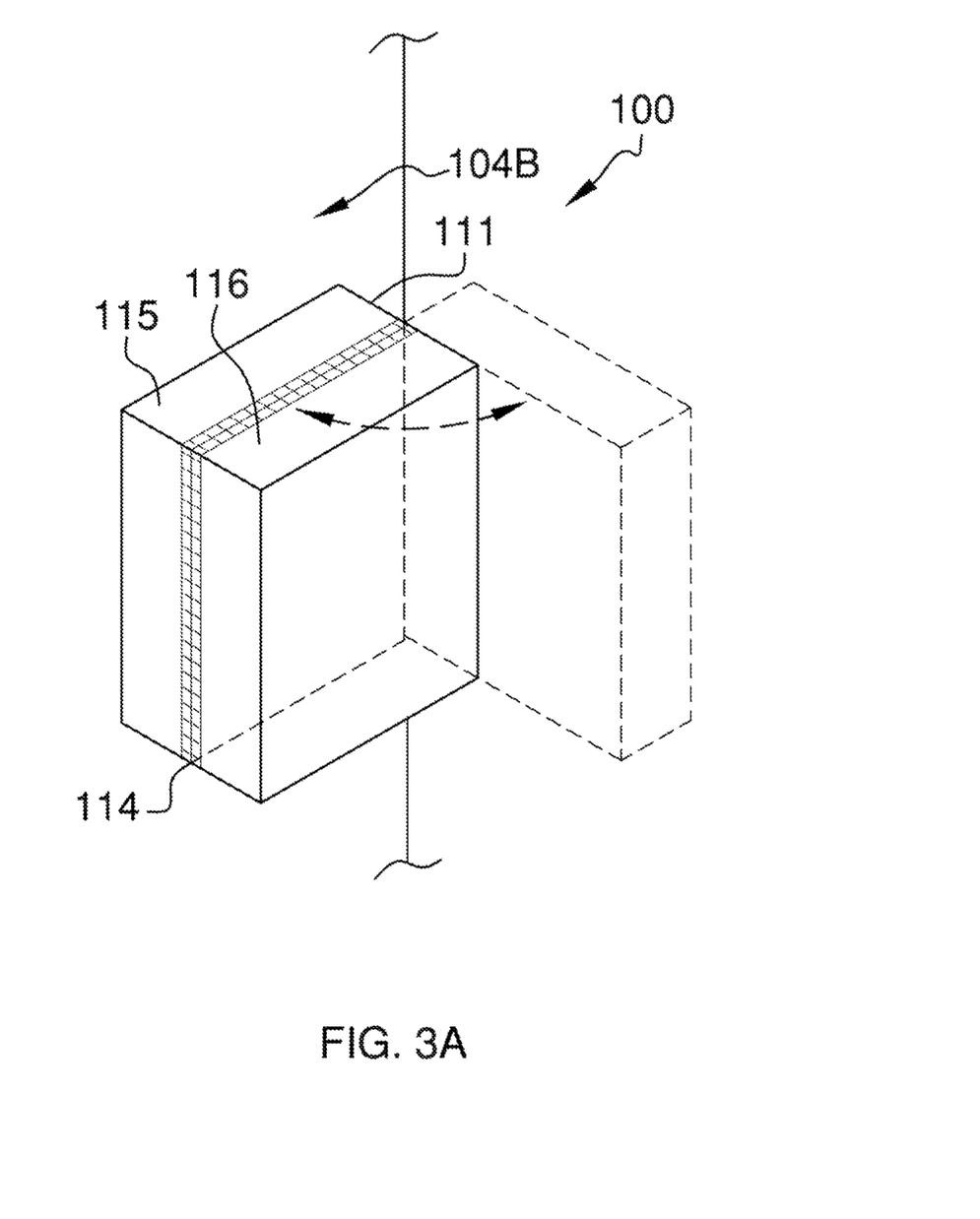
FIG. 3A illustrates a detail of the collapsible cooler in which the collapsible cooler is closed, but with depiction of the opening of the collapsible cooler.
Figure 3B:
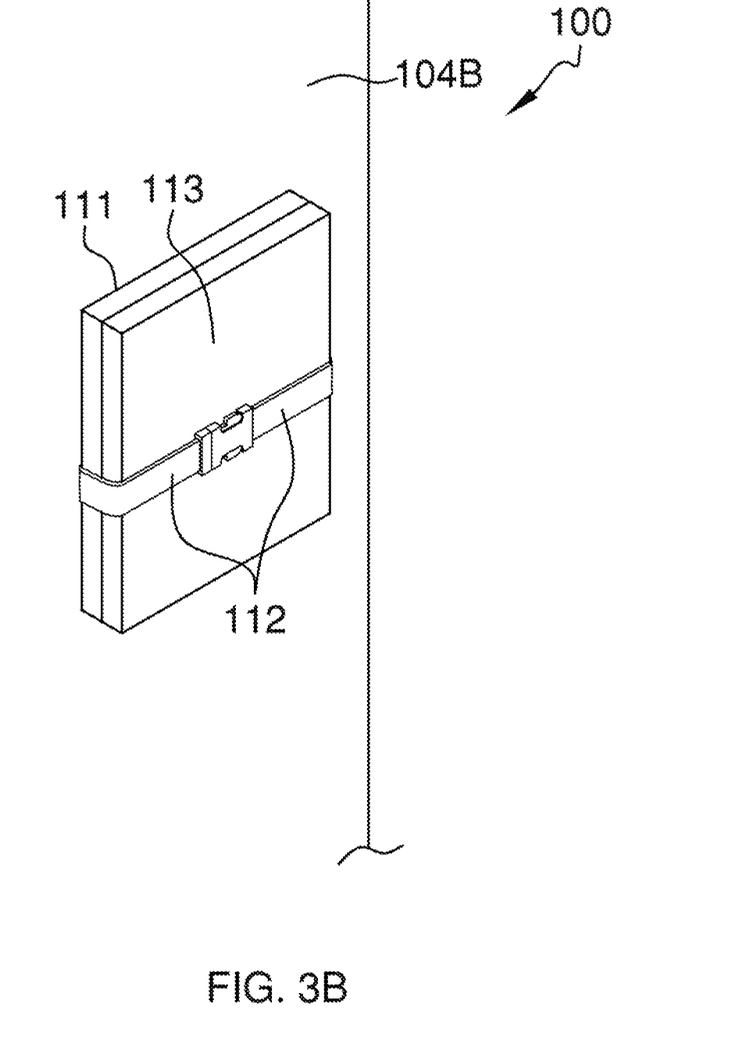
FIG. 3B illustrates the straps used to fully collapse the collapsible cooler.
Figure 4:
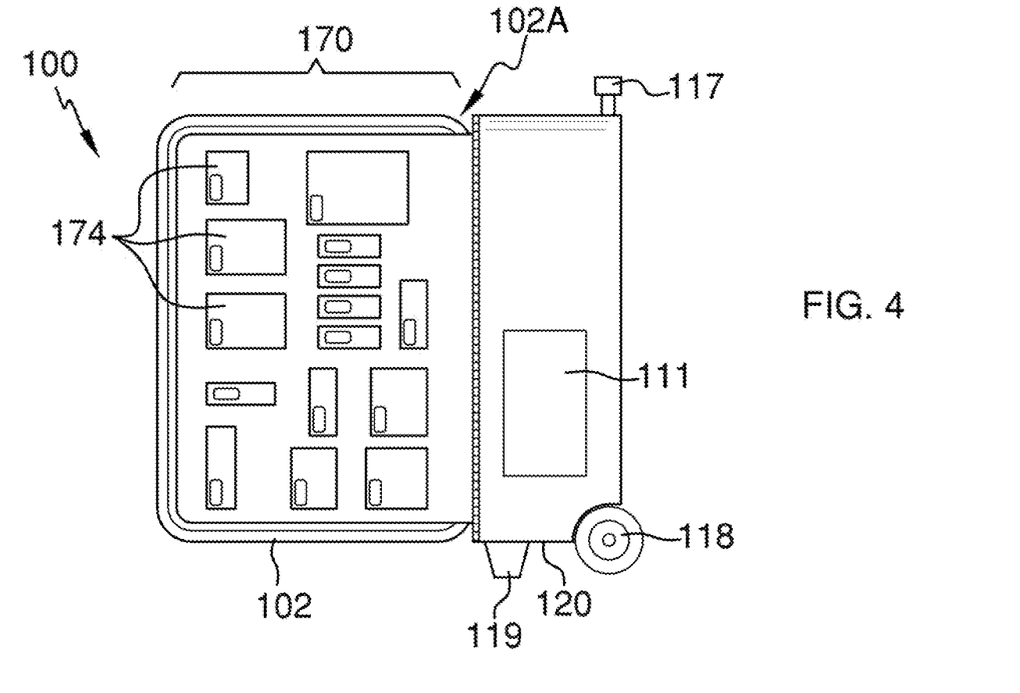
FIG. 4 illustrates a side view of the nurse's travel bag opened.

Referring to FIG. 3A, a detail of the collapsible cooler 111 is provided, and details how the collapsible cooler 111 opens to provide access to the interior of the collapsible cooler 111. FIG. 3B illustrates how the collapsible cooler 111 collapses via a pair of straps 112, which extend around to an outer surface 113 of the collapsible cooler 111. The straps 112 collapse the collapsible cooler 111, and upon disconnection of the straps 112, the collapsible cooler 111 shall extend outwardly to the shape as depicted in FIG. 3.

It shall be noted that the collapsible cooler 111 includes a zipper 114 that travels between a first cooler member 115 and a second cooler member 116, and which enables the collapsible cooler 111 to open as in FIG. 3A.

The invention 100 also includes a telescoping handle 117 and a pair of roller wheel assemblies 118. The roller wheel assemblies 118 enable the invention 100 to roll on the ground while the telescoping handle 117 enables an end user to pull the invention 100. Feet 119 are included on a bottom surface 120 of the suitcase 101, and enable the suitcase 101 to rest upright when not in motion. The pair of feet 119 are adjacent to the roller wheel assemblies 118. It shall be noted that the telescoping handle 117 extends from a top surface 121 of the suitcase 101.

Located in the interior 105 of the suitcase 101 is a plurality of dividers 170. The dividers 170 attach along the side edge 102A along with the front surface 102. The dividers 170 collectively form a plurality of compartment zones 171 within the interior 105 of the suitcase 101. The dividers 170 are each defined by a front divider surface 172 and a rear divider surface 173. Located on both the front divider surface 172 and the rear divider surface 173 is a plurality of storage compartments 174.

Figure 5:
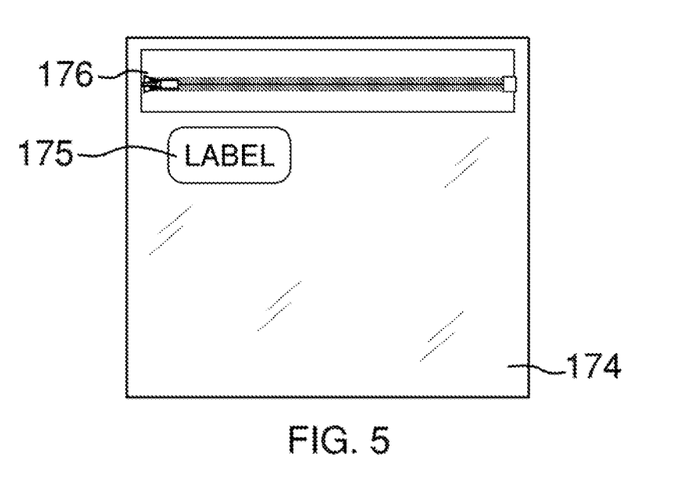
FIG. 5 illustrates an individual pocket of the nurse's travel bag in which the label is affixed to a front surface, and a zippered opening providing access therein.

Each storage compartment 174 includes a label 175 and is directed to storing a particular medical supply. Each storage compartment 174 may include a zippered opening 176 that opens and closes of the respective storage compartment. It shall be noted that the storage compartment 174 may be of clear construction such that the contents stored within the storage compartment are visible outside of the storage compartment 174.

Figure 6:
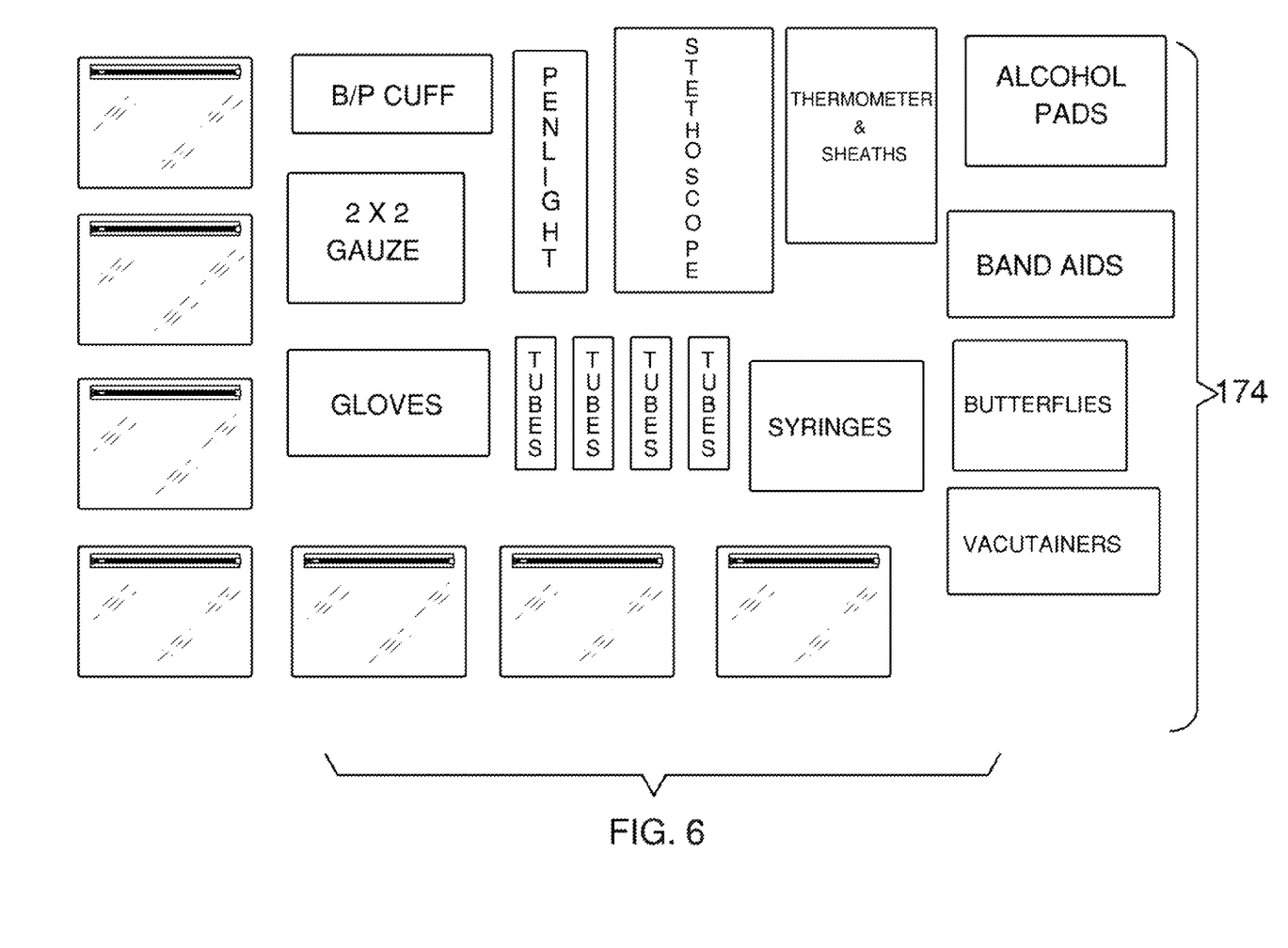
FIG. 6 illustrates the various pocket labels used as well as may clear pouches that may be included for use therein.

It shall be noted that the storage compartments 174 are arranged according to the respective medical supply, and are grouped by the different compartment zones 171. Moreover, the different medical supplies may include Band Aids, Alcohol Pads, Thermometers, Vacutainers, Butterflies, Syringes, Gloves, Gauze Pads, Pen Light, Stethoscope, etc.

The different compartment zones 171 can be arranged to particular supplies. A second compartment zone 171A may include storage compartments 174 that store a glucometer, footcare supplies, and a plurality of extra compartments of different sizes. A third compartment zone 171B may include storage compartments 174 that store a compartment for a variety of different sized gauzes, Kerlix, Ace bandages, coban, medical tape, medical scissors, small trash bags, Q-tips, tongue blades, sterile normal saline, and wound measurement rulers. A fourth compartment zone 171C may include storage compartments 174 that store paper work, a clipboard, patient folders, extra forms, a calculator, pens, and pencils.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

The inventor claims:

1. A medical supply travel bag comprising:
   a suitcase defined by a front surface, a rear surface, a bottom surface, a top surface, and opposing side surfaces;
   wherein an interior of the suitcase is adorned with a plurality of dividers that form a plurality of compartment zones in said interior;
   wherein each compartment zone of the suitcase is directed to providing a plurality of medical supplies, devices, or a particular medical need;
   wherein each divider is adorned with a plurality of storage compartments;
   wherein each pocket is suited for a specific medical supply, device;
   wherein a zipper extends along 3 of the four edges defining the front surface, and unzips to enable the front surface to rotate outwardly with respect to the remaining portions of the suitcase, and thereby enabling access to the interior; wherein the front surface is permanently affixed along a side edge to the respective opposing side surface;
   wherein the dividers attach along the side edge, and can rotate therefrom to provide access to a front divider surface or a rear divider surface;
   wherein the front surface includes a name label and a front pocket;
   wherein the rear surface includes a rear pocket for storage of a laptop computer therein;
   wherein the opposing side surfaces are further defined as a first opposing side surface and a second opposing side surface; wherein the first opposing side surface includes a sharps container; wherein the second opposing side surface includes a collapsible cooler;
   wherein the collapsible cooler extends outwardly from the second opposing side surface, wherein a pair of straps extend around an outer surface of the collapsible cooler in order to collapse the collapsible cooler when not in use;
   wherein the collapsible cooler includes a zipper that travels between a first cooler member and a second cooler member, and which enables the collapsible cooler to open.

2. The medical supply travel bag as described in claim 1 wherein a telescoping handle extends from a top surface of the suitcase while a pair of roller wheel assemblies adorn the bottom surface of the suitcase, and which enable the suitcase to be rolled upon a ground surface; wherein a pair of feet is included on the bottom surface of the suitcase, and are adjacent to the roller wheel assemblies.

3. A medical supply travel bag comprising:
   a suitcase defined by a front surface, a rear surface, a bottom surface, a top surface, and opposing side surfaces;
   wherein an interior of the suitcase is adorned with a plurality of dividers that form a plurality of compartment zones in said interior;
   wherein each compartment zone of the suitcase is directed to providing a plurality of medical supplies, devices, or a particular medical need;
   wherein each divider is adorned with a plurality of storage compartments;
   wherein each pocket is suited for a specific medical supply, device;
   wherein a zipper extends along 3 of the four edges defining the front surface, and unzips to enable the front surface to rotate outwardly with respect to the remaining portions of the suitcase, and thereby enabling access to the interior; wherein the front surface is permanently affixed along a side edge to the respective opposing side surface;
   wherein the dividers attach along the side edge, and can rotate therefrom to provide access to a front divider surface or a rear divider surface;
   wherein the front surface includes a name label and a front pocket;
   wherein the rear surface includes a rear pocket for storage of a laptop computer therein;
   wherein the opposing side surfaces are further defined as a first opposing side surface and a second opposing side surface; wherein the first opposing side surface includes a sharps container; wherein the second opposing side surface includes a collapsible cooler;
   wherein the collapsible cooler extends outwardly from the second opposing side surface, wherein a pair of straps extend around an outer surface of the collapsible cooler in order to collapse the collapsible cooler when not in use.

4. The medical supply travel bag as described in claim 3 wherein the collapsible cooler includes a zipper that travels between a first cooler member and a second cooler member, and which enables the collapsible cooler to open.

5. The medical supply travel bag as described in claim 3 wherein a telescoping handle extends from a top surface of the suitcase while a pair of roller wheel assemblies adorn the bottom surface of the suitcase, and which enable the suitcase to be rolled upon a ground surface; wherein a pair of feet is included on the bottom surface of the suitcase, and are adjacent to the roller wheel assemblies.

* * * * *